US010219718B2

(12) United States Patent
Cao et al.

(10) Patent No.: US 10,219,718 B2
(45) Date of Patent: Mar. 5, 2019

(54) ATRIAL ARRHYTHMIA EPISODE DETECTION IN A CARDIAC MEDICAL DEVICE

(71) Applicant: Medtronic, Inc., Minneapolis, MN (US)

(72) Inventors: Jian Cao, Shoreview, MN (US); Elise Higgins, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 127 days.

(21) Appl. No.: 14/520,938

(22) Filed: Oct. 22, 2014

(65) Prior Publication Data
US 2016/0113577 A1    Apr. 28, 2016

(51) Int. Cl.
*A61B 5/046* (2006.01)
*A61B 5/04* (2006.01)
*A61N 1/39* (2006.01)

(52) U.S. Cl.
CPC .......... *A61B 5/046* (2013.01); *A61B 5/04012* (2013.01); *A61N 1/3962* (2013.01)

(58) Field of Classification Search
None
See application file for complete search history.

(56) References Cited

U.S. PATENT DOCUMENTS

| | | |
|---|---|---|
| 5,292,338 A | 3/1994 | Bardy |
| 5,334,221 A | 8/1994 | Bardy |
| 5,545,186 A | 8/1996 | Olson et al. |
| 5,609,157 A | 3/1997 | Panescu |
| 5,755,739 A | 5/1998 | Sun |
| 5,782,888 A | 7/1998 | Sun |
| 5,817,134 A | 10/1998 | Greenhut |
| 6,470,210 B1 | 10/2002 | Chen et al. |
| 6,516,225 B1 | 2/2003 | Florio |
| 6,865,414 B1 | 3/2005 | Levine |
| 6,895,272 B2 | 5/2005 | Seim et al. |
| 6,904,319 B2 | 6/2005 | Seim et al. |
| 6,922,584 B2 | 7/2005 | Wang et al. |
| 6,931,273 B2 | 8/2005 | Groenewegen et al. |

(Continued)

FOREIGN PATENT DOCUMENTS

WO    01/80042 A1    10/2001

OTHER PUBLICATIONS (PCT/US2015/056593) PCT Notification of Transmittal of the International Search Report and the Written Opinion of the International Searching Authority, dated Jan. 22, 2016, 10 pages.

(Continued)

*Primary Examiner* — Erica S Lee

(57) ABSTRACT

A method and medical device for determining a cardiac episode that includes sensing a cardiac signal, identifying the signal sensed during a predetermined time interval as one of a cardiac event, a non-cardiac event, and an unclassified event, determining a number of identified cardiac events, determining a number of identified unclassified events, and determining whether the cardiac episode is occurring in response to the number of identified cardiac events being greater than a cardiac event count threshold and the number of identified unclassified events being less than an unclassified event count threshold.

18 Claims, 9 Drawing Sheets

(56) References Cited

U.S. PATENT DOCUMENTS

| | | | |
|---|---|---|---|
| 7,085,601 B1* | 8/2006 | Bardy | A61N 1/39 607/5 |
| 7,120,485 B2 | 10/2006 | Glass et al. | |
| 7,139,604 B1 | 11/2006 | Mouchawar | |
| 7,187,965 B2 | 3/2007 | Bischoff et al. | |
| 7,308,308 B1 | 12/2007 | Xi et al. | |
| 7,412,282 B2 | 8/2008 | Houben | |
| 7,509,160 B2 | 3/2009 | Bischoff et al. | |
| 7,515,956 B2 | 4/2009 | Thompson | |
| 7,532,928 B2 | 5/2009 | Lang | |
| 7,537,569 B2 | 5/2009 | Sarkar et al. | |
| 7,570,990 B2 | 8/2009 | Faber | |
| 7,580,748 B2 | 8/2009 | Garner | |
| 7,593,766 B2 | 9/2009 | Faber | |
| 7,596,405 B2 | 9/2009 | Kurzweil et al. | |
| 7,623,911 B2 | 11/2009 | Sarkar et al. | |
| 7,657,305 B2 | 2/2010 | Nigam | |
| 7,657,307 B2 | 2/2010 | Van Dam et al. | |
| 7,729,754 B2 | 6/2010 | Cao et al. | |
| 8,000,778 B2 | 8/2011 | Seim et al. | |
| 8,064,998 B2 | 11/2011 | Good | |
| 8,195,280 B2 | 6/2012 | Van Dam et al. | |
| 8,233,980 B2 | 7/2012 | Pei | |
| 8,265,753 B2 | 9/2012 | Higham | |
| 8,280,510 B2 | 10/2012 | Dyjach | |
| 8,285,377 B2 | 10/2012 | Rosenberg | |
| 8,412,316 B2 | 4/2013 | Seim et al. | |
| 8,428,705 B2 | 4/2013 | Kurzweil et al. | |
| 8,560,058 B2 | 10/2013 | Babaeizadeh | |
| 8,639,316 B2 | 1/2014 | Sarkar et al. | |
| 8,718,750 B2 | 5/2014 | Lian | |
| 2002/0147408 A1* | 10/2002 | Chen | A61N 1/3962 600/513 |
| 2005/0080347 A1* | 4/2005 | Sheth | A61B 5/046 600/515 |
| 2006/0074331 A1* | 4/2006 | Kim | A61B 5/04525 600/515 |
| 2006/0079797 A1 | 4/2006 | Bischoff et al. | |
| 2006/0079798 A1 | 4/2006 | Bischoff et al. | |
| 2006/0106323 A1 | 5/2006 | Bischoff et al. | |
| 2006/0116732 A1 | 6/2006 | Gunderson et al. | |
| 2008/0082014 A1 | 4/2008 | Cao et al. | |
| 2008/0147133 A1 | 6/2008 | Garner | |
| 2008/0154318 A1 | 6/2008 | Albus | |
| 2009/0270747 A1 | 10/2009 | van Dam et al. | |
| 2009/0275849 A1 | 11/2009 | Stewart | |
| 2011/0245699 A1 | 10/2011 | Snell et al. | |
| 2011/0319949 A1 | 12/2011 | Bardy | |
| 2012/0095520 A1* | 4/2012 | Zhang | A61B 5/0422 607/15 |

OTHER PUBLICATIONS (PCT/US2015/056599) PCT Notification of Transmittal of the International Search Report and the Written Opinion of the International Searching Authority, dated Jan. 25, 2016, 10 pages.

(PCT/US2015/056600) PCT Notification of Transmittal of the International Search Report and the Written Opinion of the International Searching Authority, dated Jan. 25, 2016, 10 pages.

Non-Final Office Action, U.S. Appl. No. 14/520,798, dated Feb. 26, 2016, 20 pages.

Response to OA for U.S. Appl. No. 14/520,798, filed May 26, 2016, 14 pages.

Non-Final Office Action for U.S. Appl. No. 14/520,847, dated May 18, 2016, 16 pages.

Final Office Action dated Nov. 23, 2016, U.S. Appl. No. 14/520,847, 14 pages.

Response to Office Action filed Aug. 18, 2016, U.S. Appl. No. 14/520,847, 13 pages.

Final Office Action mailed Nov. 23, 2016, U.S. Appl. No. 14/520,847, 13 pages.

* cited by examiner

ATRIAL ARRHYTHMIA EPISODE DETECTION IN A CARDIAC MEDICAL DEVICE

TECHNICAL FIELD

The disclosure relates generally to cardiac medical devices and, in particular, to methods for detecting atrial arrhythmia episodes during ventricular pacing in a cardiac medical device.

BACKGROUND

During normal sinus rhythm (NSR), the heart beat is regulated by electrical signals produced by the sino-atrial (SA) node located in the right atrial wall. Each atrial depolarization signal produced by the SA node spreads across the atria, causing the depolarization and contraction of the atria, and arrives at the atrioventricular (A-V) node. The A-V node responds by propagating a ventricular depolarization signal through the bundle of His of the ventricular septum and thereafter to the bundle branches and the Purkinje muscle fibers of the right and left ventricles.

Atrial tachyarrhythmia includes the disorganized form of atrial fibrillation and varying degrees of organized atrial tachycardia, including atrial flutter. Atrial fibrillation (AF) occurs because of multiple focal triggers in the atrium or because of changes in the substrate of the atrium causing heterogeneities in conduction through different regions of the atria. The ectopic triggers can originate anywhere in the left or right atrium or pulmonary veins. The AV node will be bombarded by frequent and irregular atrial activations but will only conduct a depolarization signal when the AV node is not refractory. The ventricular cycle lengths will be irregular and will depend on the different states of refractoriness of the AV-node.

As more serious consequences of persistent atrial arrhythmias have come to be understood, such as an associated risk of relatively more serious ventricular arrhythmias and stroke, there is a growing interest in monitoring and treating atrial arrhythmias.

Methods for discriminating arrhythmias that are atrial in origin from arrhythmias originating in the ventricles have been developed for use in dual chamber implantable devices wherein both an atrial EGM signal and a ventricular EGM signal are available. Discrimination of arrhythmias can rely on event intervals (PP intervals and RR intervals), event patterns, and EGM morphology. Such methods have been shown to reliably discriminate ventricular arrhythmias from supra-ventricular arrhythmias. In addition, such methods have been developed for use in single chamber implantable devices, subcutaneous implantable devices, and external monitoring devices, where an adequate atrial EGM signal having acceptable signal-to-noise ratio is not always available for use in detecting and discriminating atrial arrhythmias. However, such single chamber devices have been designed to monitor AF during non-paced ventricular rhythm. What is needed, therefore, is a method for monitoring atrial arrhythmias during a ventricular paced rhythm.

DETAILED DESCRIPTION

In the following description, references are made to illustrative embodiments for carrying out the methods described herein. It is understood that other embodiments may be utilized without departing from the scope of the disclosure.

In various embodiments, ventricular signals are used for determining successive ventricular cycle lengths for use in detecting atrial arrhythmias. The atrial arrhythmia detection methods do not require an atrial signal source. The methods presented herein may be embodied in software, hardware or firmware in implantable or external medical devices. Such devices include implantable monitoring devices having cardiac EGM/ECG monitoring capabilities and associated EGM/ECG sense electrodes, which may be intracardiac, epicardial, or subcutaneous electrodes.

The methods described herein can also be incorporated in implantable medical devices having therapy delivery capabilities, such as single chamber or bi-ventricular pacing systems or ICDs that sense the R-waves in the ventricles and deliver an electrical stimulation therapy to the ventricles. The atrial arrhythmia detection methods presently disclosed may also be incorporated in external monitors having ECG electrodes coupled to the patient's skin to detect R-waves, e.g. Holter monitors, or within computerized systems that analyze pre-recorded ECG or EGM data. Embodiments may further be implemented in a patient monitoring system, such as a centralized computer system which processes data sent to it by implantable or wearable monitoring devices.

Figure 1:
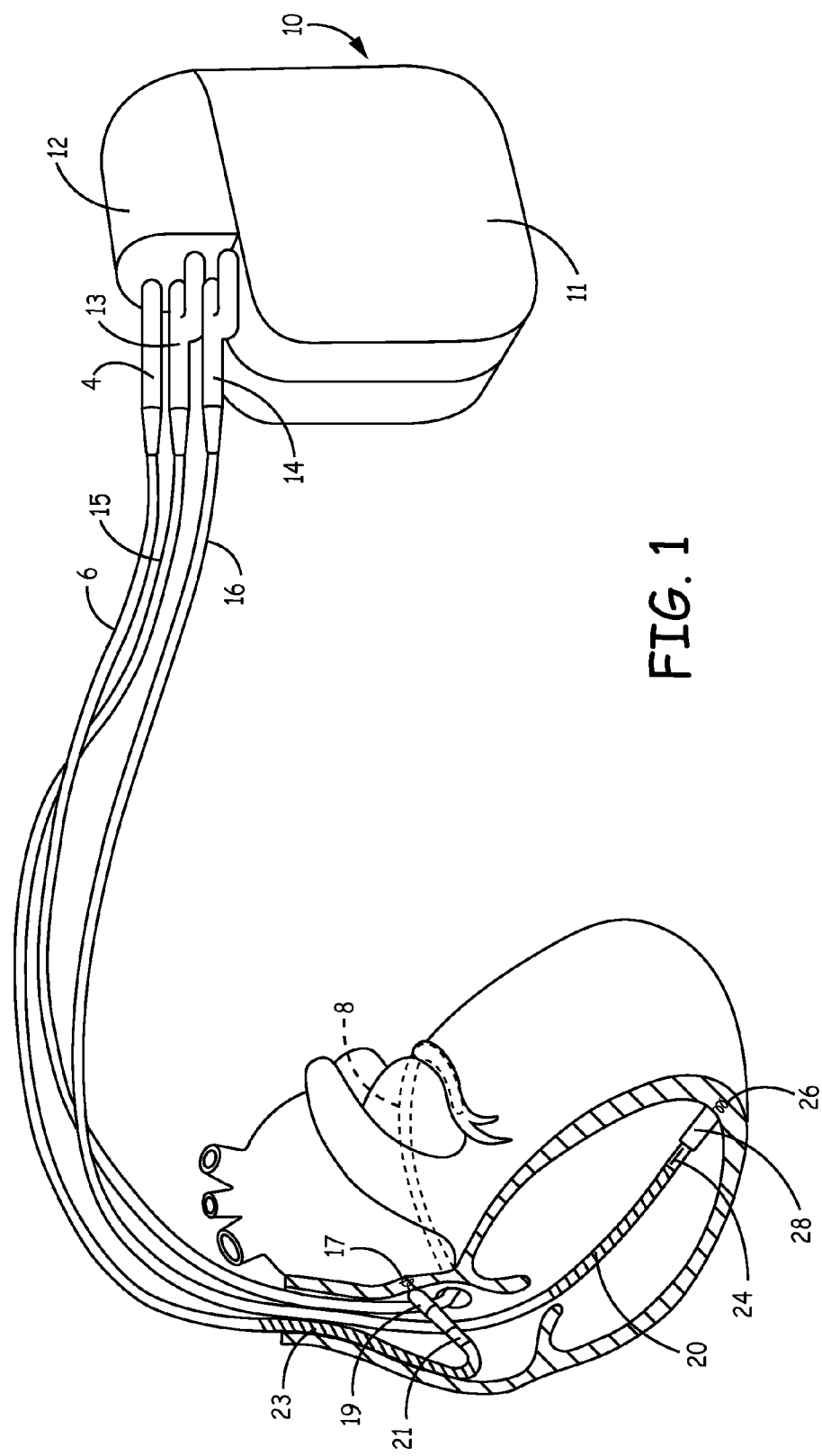
FIG. 1 is a schematic diagram of an exemplary medical device for detecting arrhythmia during ventricular pacing according to an embodiment of the present disclosure.

FIG. 1 is a schematic diagram of an exemplary medical device for detecting arrhythmia during ventricular pacing according to an embodiment of the present disclosure. As illustrated in FIG. 1, a medical device according to an embodiment of the present disclosure may be in the form of an implantable cardioverter defibrillator (ICD) 10 a connector block 12 that receives the proximal ends of a right ventricular lead 16, a right atrial lead 15 and a coronary sinus lead 6, used for positioning electrodes for sensing and stimulation in three or four heart chambers. Right ventricular lead 16 is positioned such that its distal end is in the right ventricle for sensing right ventricular cardiac signals and delivering pacing or shocking pulses in the right ventricle. For these purposes, right ventricular lead 16 is equipped with a ring electrode 24, an extendable helix electrode 26 mounted retractably within an electrode head 28, and a coil electrode 20, each of which are connected to an insulated conductor within the body of lead 16. The proximal end of the insulated conductors are coupled to corresponding connectors carried by bifurcated connector 14 at the proximal end of lead 16 for providing electrical connection to the ICD 10. It is understood that although the device illustrated in FIG. 1 is a dual chamber device, other devices such as single chamber devices may be utilized to perform the technique of the present disclosure described herein.

The right atrial lead 15 is positioned such that its distal end is in the vicinity of the right atrium and the superior vena cava. Lead 15 is equipped with a ring electrode 21 and an extendable helix electrode 17, mounted retractably within electrode head 19, for sensing and pacing in the right atrium. Lead 15 is further equipped with a coil electrode 23 for delivering high-energy shock therapy. The ring electrode 21, the helix electrode 17 and the coil electrode 23 are each connected to an insulated conductor with the body of the right atrial lead 15. Each insulated conductor is coupled at its proximal end to a connector carried by bifurcated connector 13.

The coronary sinus lead 6 is advanced within the vasculature of the left side of the heart via the coronary sinus and great cardiac vein. The coronary sinus lead 6 is shown in the embodiment of FIG. 1 as having a defibrillation coil electrode 8 that may be used in combination with either the coil electrode 20 or the coil electrode 23 for delivering electrical shocks for cardioversion and defibrillation therapies. In other embodiments, coronary sinus lead 6 may also be equipped with a distal tip electrode and ring electrode for pacing and sensing functions in the left chambers of the heart. The coil electrode 8 is coupled to an insulated conductor within the body of lead 6, which provides connection to the proximal connector 4.

The electrodes 17 and 21 or 24 and 26 may be used as true bipolar pairs, commonly referred to as a "tip-to-ring" configuration. Further, electrode 17 and coil electrode 20 or electrode 24 and coil electrode 23 may be used as integrated bipolar pairs, commonly referred to as a "tip-to-coil" configuration. In accordance with the invention, ICD 10 may, for example, adjust the electrode configuration from a tip-to-ring configuration, e.g., true bipolar sensing, to a tip-to-coil configuration, e.g., integrated bipolar sensing, upon detection of oversensing in order to reduce the likelihood of future oversensing. In other words, the electrode polarities can be reselected in response to detection of oversensing in an effort to reduce susceptibility of oversensing. In some cases, electrodes 17, 21, 24, and 26 may be used individually in a unipolar configuration with the device housing 11 serving as the indifferent electrode, commonly referred to as the "can" or "case" electrode.

The device housing 11 may also serve as a subcutaneous defibrillation electrode in combination with one or more of the defibrillation coil electrodes 8, 20 or 23 for defibrillation of the atria or ventricles. It is recognized that alternate lead systems may be substituted for the three lead system illustrated in FIG. 1. While a particular multi-chamber ICD and lead system is illustrated in FIG. 1, methodologies included in the present invention may adapted for use with any single chamber, dual chamber, or multi-chamber ICD or pacemaker system, subcutaneous implantable device, or other internal or external cardiac monitoring device.

Figure 2:
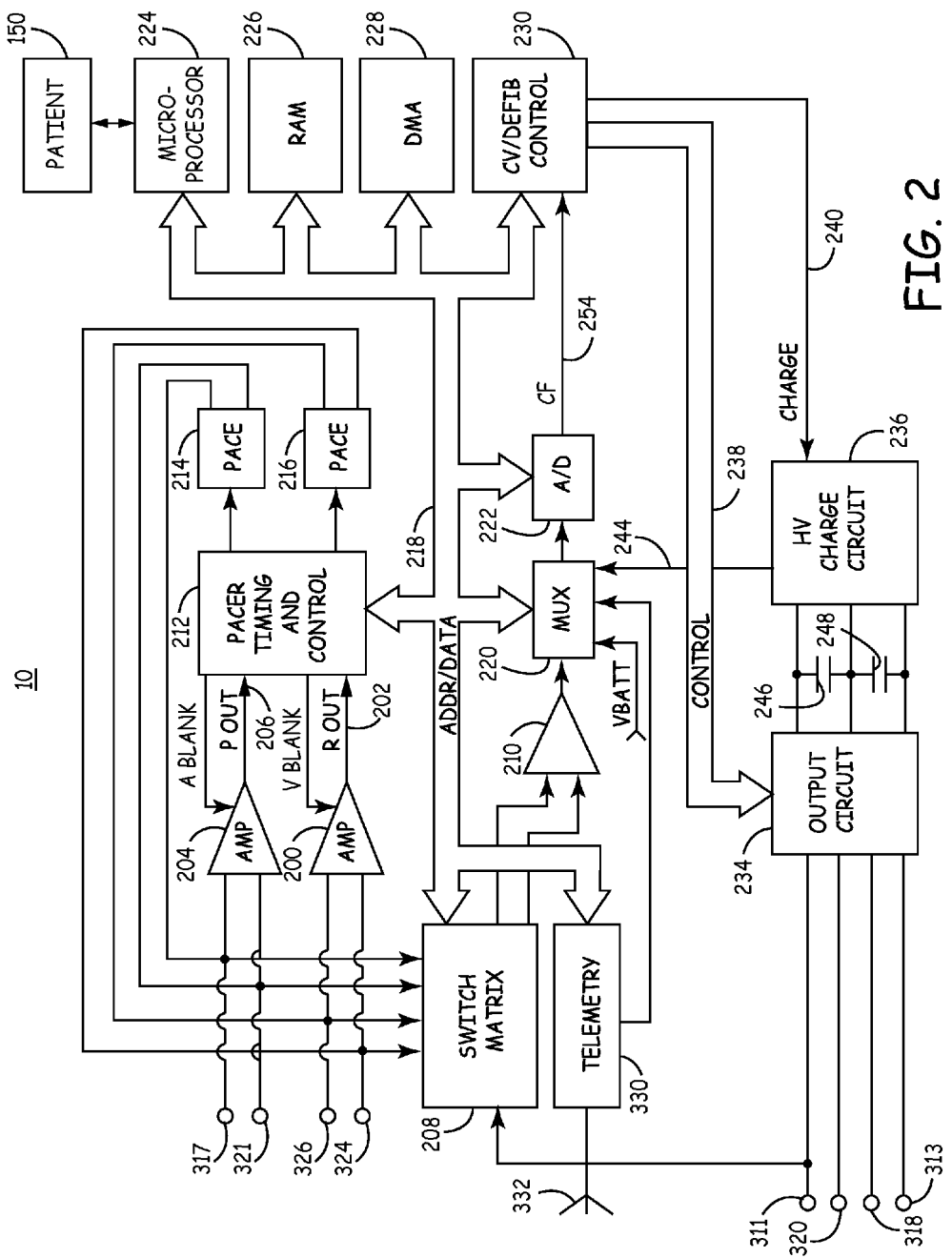
FIG. 2 is a functional block diagram of an IMD according to one embodiment.

FIG. 2 is a functional schematic diagram of the medical device of FIG. 1. This diagram should be taken as exemplary of the type of device with which the invention may be embodied and not as limiting. The disclosed embodiment shown in FIG. 2 is a microprocessor-controlled device, but the methods of the present invention may also be practiced with other types of devices such as those employing dedicated digital circuitry.

With regard to the electrode system illustrated in FIG. 1, ICD 10 is provided with a number of connection terminals for achieving electrical connection to the leads 6, 15, and 16 and their respective electrodes. A connection terminal 311 provides electrical connection to the housing 11 for use as the indifferent electrode during unipolar stimulation or sensing. The connection terminals 320, 313, and 318 provide electrical connection to coil electrodes 20, 8 and 23 respectively. Each of these connection terminals 311, 320, 313, and 318 are coupled to the high voltage output circuit 234 to facilitate the delivery of high energy shocking pulses to the heart using one or more of the coil electrodes 8, 20, and 23 and optionally the housing 11.

The connection terminals 317 and 321 provide electrical connection to the helix electrode 17 and the ring electrode 21 positioned in the right atrium. The connection terminals 317 and 321 are further coupled to an atrial sense amplifier 204 for sensing atrial signals such as P-waves. The connection terminals 326 and 324 provide electrical connection to the helix electrode 26 and the ring electrode 24 positioned in the right ventricle. The connection terminals 326 and 324 are further coupled to a ventricular sense amplifier 200 for sensing ventricular signals. The atrial sense amplifier 204 and the ventricular sense amplifier 200 preferably take the form of automatic gain controlled amplifiers with adjustable sensitivity. In accordance with the invention, ICD 10 and, more specifically, microprocessor 224 automatically adjusts the sensitivity of atrial sense amplifier 204, ventricular sense amplifier 200 or both in response to detection of oversensing in order to reduce the likelihood of oversensing. Ventricular sense amplifier 200 and atrial sense amplifier 204 operate in accordance with originally programmed sensing parameters for a plurality of cardiac cycles, and upon detecting oversensing, automatically provides the corrective action to avoid future oversensing. In this manner, the adjustments provided by ICD 10 to amplifiers 200 and 204 to avoid future oversensing are dynamic in nature. Particularly, microprocessor 224 increases a sensitivity value of the amplifiers, thus reducing the sensitivity, when oversensing is detected. Atrial sense amplifier 204 and ventricular sense amplifier 200 receive timing information from pacer timing and control circuitry 212.

Specifically, atrial sense amplifier 204 and ventricular sense amplifier 200 receive blanking period input, e.g., ABLANK and VBLANK, respectively, which indicates the amount of time the electrodes are "turned off" in order to prevent saturation due to an applied pacing pulse or defibrillation shock. As will be described, the blanking periods of atrial sense amplifier 204 and ventricular sense amplifier 200 and, in turn, the blanking periods of sensing electrodes associated with the respective amplifiers may be automatically adjusted by ICD 10 to reduce the likelihood of oversensing. The general operation of the ventricular sense amplifier 200 and the atrial sense amplifier 204 may correspond to that disclosed in U.S. Pat. No. 5,117,824, by Keimel, et al., incorporated herein by reference in its entirety. Whenever a signal received by atrial sense amplifier 204 exceeds an atrial sensitivity, a signal is generated on the P-out signal line 206. Whenever a signal received by the ventricular sense amplifier 200 exceeds a ventricular sensitivity, a signal is generated on the R-out signal line 202.

Switch matrix 208 is used to select which of the available electrodes are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion and defibrillation functions of the ICD 10. Specifically, microprocessor 224 may modify the electrode configurations based on detection of oversensing due to cardiac or non-cardiac origins. Upon detection of R-wave oversensing, for example, microprocessor 224 may modify the electrode configuration of the right ventricle from true bipolar sensing, e.g., tip-to-ring, to integrated bipolar sensing, e.g., tip-to-coil.

Signals from the electrodes selected for coupling to bandpass amplifier 210 are provided to multiplexer 220, and thereafter converted to multi-bit digital signals by A/D converter 222, for storage in random access memory 226 under control of direct memory access circuit 228 via data/address bus 218. Microprocessor 224 may employ digital signal analysis techniques to characterize the digitized signals stored in random access memory 226 to recognize and classify the patient's heart rhythm employing any of the numerous signal processing methodologies known in the art. An exemplary tachyarrhythmia recognition system is described in U.S. Pat. No. 5,545,186 issued to Olson et al, incorporated herein by reference in its entirety.

Upon detection of an arrhythmia, an episode of EGM data, along with sensed intervals and corresponding annotations of sensed events, are preferably stored in random access memory 226. The EGM signals stored may be sensed from programmed near-field and/or far-field sensing electrode pairs. Typically, a near-field sensing electrode pair includes a tip electrode and a ring electrode located in the atrium or the ventricle, such as electrodes 17 and 21 or electrodes 26 and 24. A far-field sensing electrode pair includes electrodes spaced further apart such as any of: the defibrillation coil electrodes 8, 20 or 23 with housing 11; a tip electrode 17 or 26 with housing 11; a tip electrode 17 or 26 with a defibrillation coil electrode 20 or 23; or atrial tip electrode 17 with ventricular ring electrode 24. The use of near-field and far-field EGM sensing of arrhythmia episodes is described in U.S. Pat. No. 5,193,535, issued to Bardy, incorporated herein by reference in its entirety. Annotation of sensed events, which may be displayed and stored with EGM data, is described in U.S. Pat. 4,374,382 issued to Markowitz, incorporated herein by reference in its entirety.

The telemetry circuit 330 receives downlink telemetry from and sends uplink telemetry to an external programmer, as is conventional in implantable anti-arrhythmia devices, by means of an antenna 332. Data to be uplinked to the programmer and control signals for the telemetry circuit are provided by microprocessor 224 via address/data bus 218. EGM data that has been stored upon arrhythmia detection or as triggered by other monitoring algorithms may be uplinked to an external programmer using telemetry circuit 330. Received telemetry is provided to microprocessor 224 via multiplexer 220. Numerous types of telemetry systems known in the art for use in implantable devices may be used.

The remainder of the circuitry illustrated in FIG. 2 is an exemplary embodiment of circuitry dedicated to providing cardiac pacing, cardioversion and defibrillation therapies. The pacer timing and control circuitry 212 includes programmable digital counters which control the basic time intervals associated with various single, dual or multi-chamber pacing modes or anti-tachycardia pacing therapies delivered in the atria or ventricles. Pacer circuitry 212 also determines the amplitude of the cardiac pacing pulses under the control of microprocessor 224.

During pacing, escape interval counters within pacer timing and control circuitry 212 are reset upon sensing of R-waves or P-waves as indicated by signals on lines 202 and 206, respectively. In accordance with the selected mode of pacing, pacing pulses are generated by atrial pacer output circuit 214 and ventricular pacer output circuit 216. The pacer output circuits 214 and 216 are coupled to the desired electrodes for pacing via switch matrix 208. The escape interval counters are reset upon generation of pacing pulses, and thereby control the basic timing of cardiac pacing functions, including anti-tachycardia pacing.

The durations of the escape intervals are determined by microprocessor 224 via data/address bus 218. The value of the count present in the escape interval counters when reset by sensed R-waves or P-waves can be used to measure R-R intervals and P-P intervals for detecting the occurrence of a variety of arrhythmias.

The microprocessor 224 includes associated read-only memory (ROM) in which stored programs controlling the operation of the microprocessor 224 reside. A portion of the random access memory (RAM) 226 may be configured as a number of recirculating buffers capable of holding a series of measured intervals for analysis by the microprocessor 224 for predicting or diagnosing an arrhythmia. In response to the detection of tachycardia, anti-tachycardia pacing therapy can be delivered by loading a regimen from microprocessor 224 into the pacer timing and control circuitry 212 according to the type of tachycardia detected. In the event that higher voltage cardioversion or defibrillation pulses are required, microprocessor 224 activates the cardioversion and defibrillation control circuitry 230 to initiate charging of the high voltage capacitors 246 and 248 via charging circuit 236 under the control of high voltage charging control line 240. The voltage on the high voltage capacitors is monitored via a voltage capacitor (VCAP) line 244, which is passed through the multiplexer 220. When the voltage reaches a predetermined value set by microprocessor 224, a logic signal is generated on the capacitor full (CF) line 254, terminating charging. The defibrillation or cardioversion pulse is delivered to the heart under the control of the pacer timing and control circuitry 212 by an output circuit 234 via a control bus 238. The output circuit 234 determines the electrodes used for delivering the cardioversion or defibrillation pulse and the pulse wave shape.

In one embodiment, the ICD 10 may be equipped with a patient notification system 150. Any patient notification method known in the art may be used such as generating perceivable twitch stimulation or an audible sound. A patient notification system may include an audio transducer that emits audible sounds including voiced statements or musical tones stored in analog memory and correlated to a programming or interrogation operating algorithm or to a warning trigger event as generally described in U.S. Pat. No. 6,067,473 issued to Greeninger et al., incorporated herein by reference in its entirety.

Figure 3:
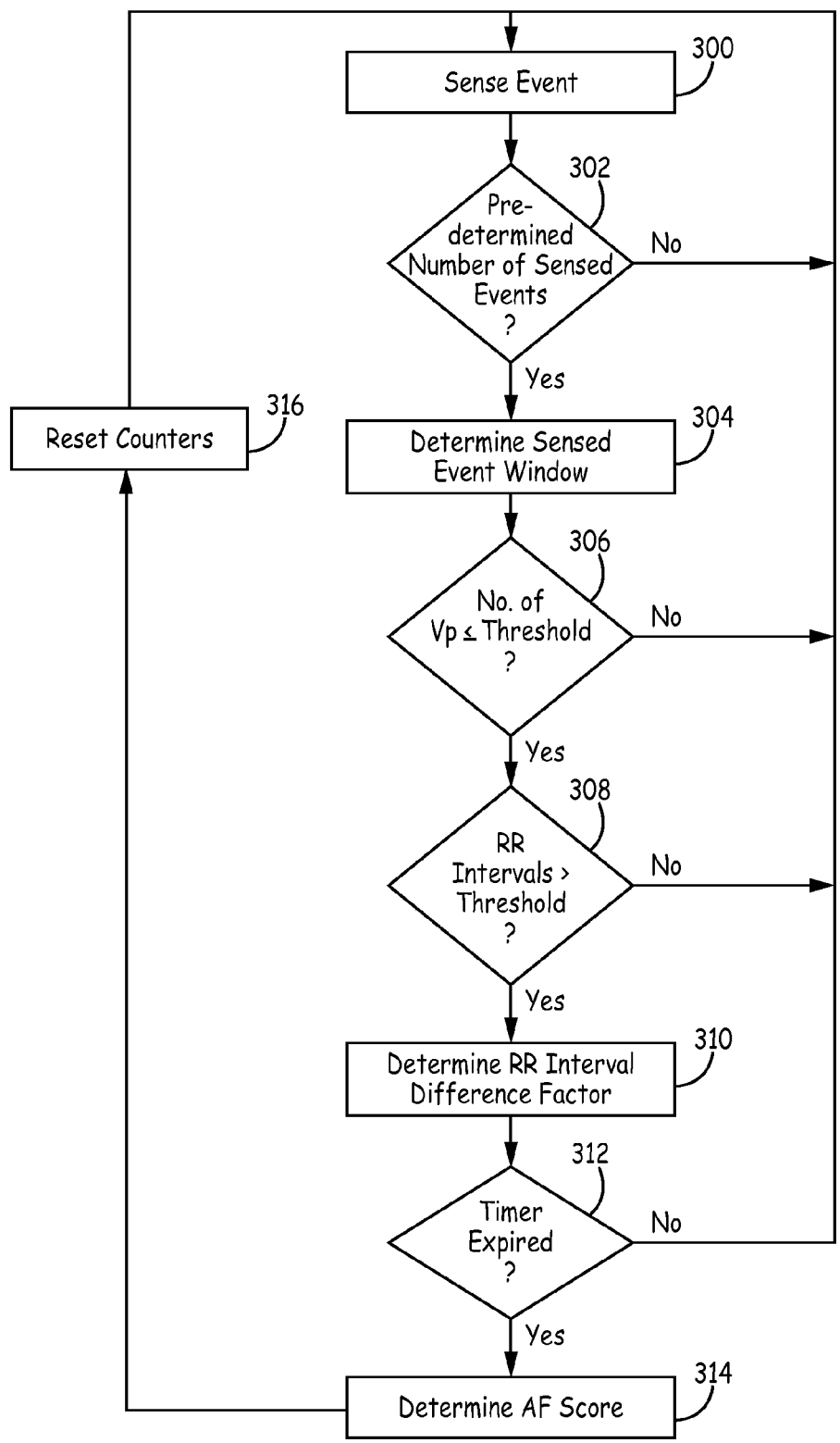
FIG. 3 is flowchart of a method for detecting atrial arrhythmias during ventricular pacing in a cardiac medical device according to an embodiment of the present disclosure.

FIG. 3 is flowchart of a method for detecting atrial arrhythmias during intermittent instances of ventricular pacing in a cardiac medical device according to an embodiment of the present disclosure. Flow chart 200 and other flow charts presented herein are intended to illustrate the functional operation of the device, and should not be construed as reflective of a specific form of software or hardware necessary to practice the invention. It is believed that the particular form of software will be determined primarily by the particular system architecture employed in the device and by the particular detection and therapy delivery methodologies employed by the device. Providing software to accomplish the present invention in the context of any modern IMD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

As illustrated in FIG. 3, during detection of atrial arrhythmias, the device senses events, such as ventricular events, for example, Block 300, and identifies the sensed ventricular event as being either an intrinsic sensed event Vs or a paced event Vp resulting from pacing being delivered by the device. Depending upon the number of RR intervals chosen for determining RR interval differences, the device determines whether a predetermined number of sensed events, either a ventricular pacing event Vp or intrinsic ventricular sensed event VS, have been sensed, Block 302. For example, according to one embodiment, if the desired number of RR intervals for RR interval differences is three, the predetermined number of sensed events utilized in Block 302 would be four sensed events, with the four sensed events forming a sensing window, as will be illustrated below. If the predetermined number of sensed events have not been sensed, the device determines the next sensed event, Block 300, and the process is repeated.

Once the predetermined number of events are sensed, Yes in Block 302, a sensed event window is identified based on the four events, Block 304, and a determination is made as to whether the number of the sensed events in the sensed event window that are ventricular pace Vp events is less than or equal to a predetermined pacing event threshold, Block 306. For example, according to one embodiment, the pacing event threshold is set as one so that the device determines whether one or less of the sensed events in the sensed event window are ventricular pace events. If the number of the sensed events in the sensed event window that are ventricular pace Vp events is not less than or equal to, i.e., is greater than the predetermined pacing event threshold, No in Block 306, the device determines the next sensed event, Block 300, and the process is repeated.

If the number of the sensed events in the sensed event window that are ventricular pace Vp events is less than or equal to the predetermined pacing event threshold, Yes in Block 306, the device determines whether each of the RR intervals associated with the sensed events in the current sensed event window are greater than a predetermined interval threshold, Block 308. For example, according to one embodiment the device determines whether each of the RR intervals associated with the sensed events in the sensed event window are greater than 220 milliseconds. If each of the RR intervals associated with the sensed events in the sensed event window are not greater than 220 milliseconds, No in Block 308, the device determines the next sensed event, Block 300, and the process is repeated using the next sensed event and the resulting next sensed event window.

If each of the RR intervals associated with the sensed events in the sensed event window are greater than 220 milliseconds, Yes in Block 308, the device determines differences or variability of the RR intervals associated with the sensed events in the sensed event window, Block 310, as will be described below. Once the RR intervals differences for the current sensed event window have been determined in Block 308, the device determines whether a predetermined cardiac event timer has expired, Block 312. If the event timer has not expired, No in Block 312, the device determines the next sensed event, Block 300, and the process is repeated using the next sensed event and the resulting next sensed event window. According to one embodiment, the cardiac event timer is set as two minutes so that once the event timer has expired, Yes in Block 312, the device determines an atrial fibrillation AF score, Block 314, based on the determined RR interval differences, Block 310, resulting from multiple sensed event windows occurring during the predetermined time period, Block 312, i.e., two minutes for example. The determination of the AF score is described below, with the device making a determining of either an atrial fibrillation AF event or a non-atrial fibrillation event occurring based on a comparison of the AF score to an AF detection threshold. The stored differences are then cleared, Block 316, and the device determines the next sensed event, Block 300, and the process is repeated for the next time period using the next sensed events and the resulting next sensed event windows.

Figure 4:
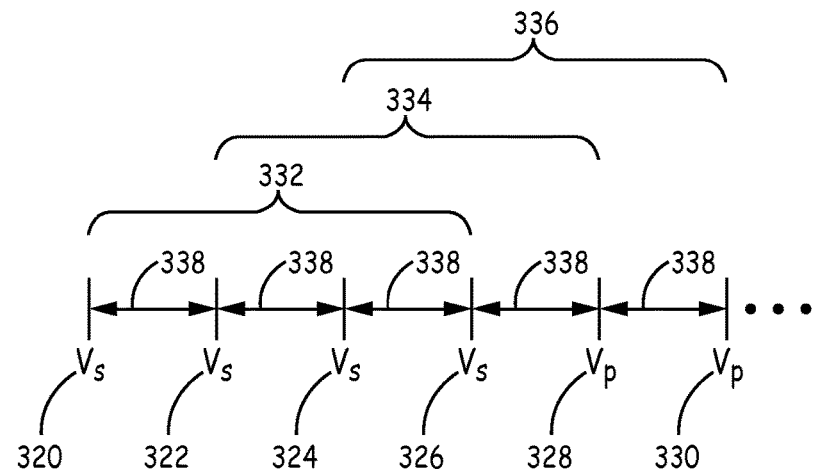
FIG. 4 is a schematic diagram illustrating detecting atrial arrhythmias during ventricular pacing in a cardiac medical device according to an embodiment of the present disclosure.

FIG. 4 is a schematic diagram illustrating detecting atrial arrhythmias during ventricular pacing in a cardiac medical device according to an embodiment of the present disclosure. As illustrated in FIGS. 3 and 4, according to one embodiment, once the device senses the predetermined number of sensed events 320-326, Yes in Block 302, a sensed event window 332 is formed, Block 304, based on the current four sensed events 320-326. The device determines whether only one or less of the sensed events 320-326 are ventricular paced events, Block 306, and whether the RR intervals 338 formed between the sensed events 320-326 are greater than the interval threshold, Block 308. In the example illustrated in FIG. 4, all of sensed events 320-326 are ventricular sensed Vs events, and assuming all of the intervals 338 formed by the sensed events 320-326 are greater than the interval threshold, Yes in Block 308, the device determines and stores an interval difference factor associated with the intervals 338 of the current sensed events 320-326, Block 310. If all of the intervals 338 formed by the sensed events 320-326 are not greater than the interval threshold, No in Block 308, the device determines the next sensed event, Block 300, and the process is repeated using the next sensed event and the resulting next sensed event window.

Assuming the cardiac event timer has not yet expired, No in Block 312, the device senses the next event 328, Block 300, and a sensed event window 334 is formed, Block 304, based on the current four sensed events 322-328. The device determines whether only one or less of the sensed events 322-328 are ventricular paced events, Block 306, and whether the RR intervals 338 formed between the sensed events 322-328 are greater than the interval threshold, Block 308. In the example illustrated in FIG. 4, since only one sensed event 338 of sensed events 322-328 is a ventricular paced Vp event, and assuming all of the intervals 338 formed by the sensed events 322-328 are greater than the interval threshold, Yes in Block 308, the device determines and stores an interval difference factor associated with the intervals 338 of the current sensed events 322-328, Block 310.

Assuming the cardiac event timer has not yet expired, No in Block 312, the device senses the next event 330, Block 300, and a sensed event window 336 is formed, Block 304, based on the current four sensed events 324-330. The device determines whether only one or less of the sensed events 324-330 are ventricular paced events, Block 306, and whether the RR intervals 338 formed between the sensed events 324-330 are greater than the interval threshold, Block 308. In the example illustrated in FIG. 4, since two sensed events 338 and 340 of sensed events 324-330 are ventricular paced Vp events, and therefore the number of sensed events in the sensed event window 336 that are ventricular paced Vp events is not less than or equal to the pacing event threshold, No in Block 306, an RR interval difference factor is not determined for that sensed event window 336, and the device determines the next sensed event, Block 300, and the process is repeated using the next sensed event and the resulting next sensed event window, and so on until the timer has expired, Yes in Block 312. Once the timer has expired, Yes in Block 312, the atrial fibrillation AF score for that time period is determined based on the currently stored interval difference factors, as described below.

Figure 5:
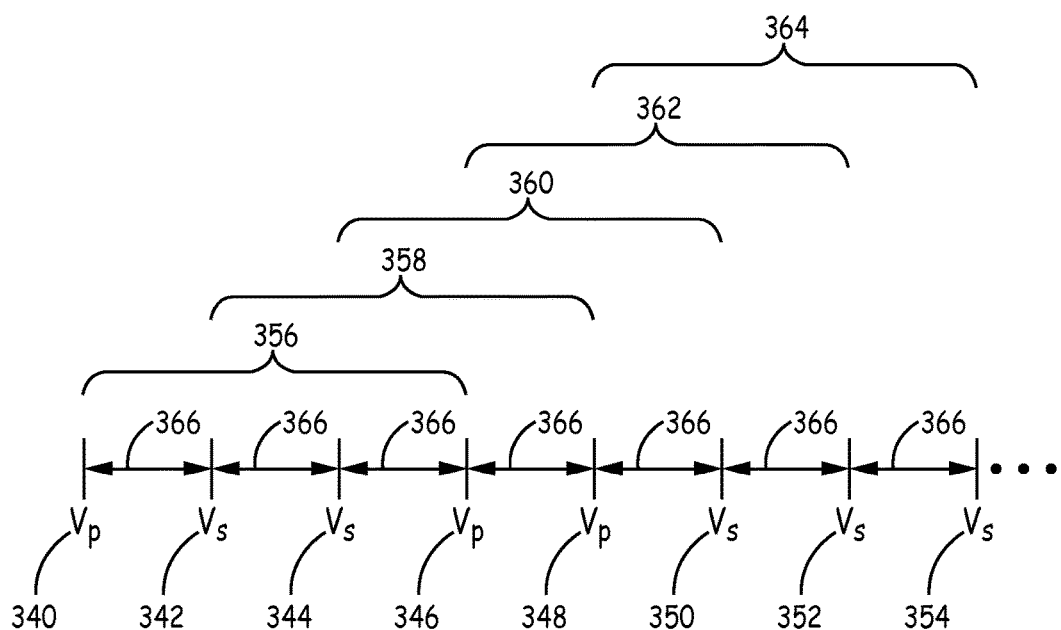
FIG. 5 is a schematic diagram illustrating detecting atrial arrhythmias during ventricular pacing in a cardiac medical device according to another embodiment of the present disclosure.

FIG. 5 is a schematic diagram illustrating detecting atrial arrhythmias during ventricular pacing in a cardiac medical device according to another embodiment of the present disclosure. As illustrated in FIGS. 3 and 5, according to another embodiment, once the device senses the predetermined number of sensed events 340-346, Yes in Block 302, a sensed event window 356 is formed, Block 304, based on the current four sensed events 340-346. The device determines whether only one or less of the sensed events 340-346 are ventricular paced Vp events, Block 306, and whether the RR intervals 366 formed between the sensed events 340-346 are greater than the interval threshold, Block 308. In the exemplary embodiment illustrated in FIG. 5, during the determination as to whether only one or less of the sensed events 340-346 are ventricular paced Vp events, Block 306, rather than making the determination based on all of the sensed events 340-346 in the sensed event window 356, the device determines whether one or more of a predetermined number of the sensed events 340-346 are ventricular pace Vp events. For example, according to one embodiment, the device may determine whether only one or less of the most recent sensed event 346 in the sensed event window 356 and the previous two sensed events 342 and 344 are ventricular sensed Vp events, Block 306.

In the example illustrated in FIG. 5, the most recent sensed event 346 in the sensed event window 356 is a ventricular pace Vp event, and the two previous sensed events 342 and 344 are both ventricular sense VS events, resulting in there being only one ventricular pace Vp event. Therefore, the number of ventricular pace VP events is determined to be less than or equal to the ventricular pace Vp event threshold, i.e., one ventricular pace Vp event, Yes in Block 306. As a result, similar to above, the device determines whether the RR intervals 366 associated with the current sensed events 340-346 are greater than an interval threshold, Block 308, such as 220 milliseconds, for example. If the RR intervals 366 are not greater than the interval threshold, No in Block 308, the device does not store an interval difference factor, Block 310, for the intervals 366 associated with the current sensed events 340-346, and the process is repeated using the next sensed event 348 and the resulting next sensed event window 358.

If each of the RR intervals 366 are greater than the interval threshold, Yes in Block 308, the device stores an interval difference factor, Block 310, associated with the intervals 366 formed between the current sensed events 340-346, described below, and, assuming the timer has not expired, No in Block 312, the process is repeated using the next sensed event 348 and the resulting next sensed event window 360. If the timer has expired, Yes in Block 312, the device determines an atrial fibrillation AF score, Block 314, based on the determined RR interval difference factors, Block 310, resulting from multiple sensed event windows over the predetermined time period of Block 312, such as two minutes, for example. The determination of the AF score is described below, with the device making a determining of either an atrial fibrillation AF event or a non-atrial fibrillation event occurring based on a comparison of the AF score to an AF detection threshold. The current counters are then cleared, Block 316, and the device determines the next sensed event, Block 300, and the process is repeated for the next time period using the next sensed events and the resulting next sensed event windows.

As described above, if the RR intervals are not greater than the interval threshold, No in Block 310, or if the cardiac event timer has not yet expired, No in Block 312, the device senses the next cardiac event 348, Block 300, and a sensed event window 358 is formed, Block 304, based on the most current four sensed events 342-348. The device determines whether only one or less of the most recent sensed event 348 in the sensed event window 358 and the previous two sensed events 344 and 346 are ventricular sensed Vp events, Block 306. In the example illustrated in FIG. 5, the most recent sensed event 348 and one sensed event 346 of the two previous sensed events 344 and 346 are ventricular pace Vp events, and the other previous sensed event 344 is a ventricular sense VS event, resulting in there being two ventricular pace Vp events. Therefore, since the number of ventricular pace VP events is not less than or equal to the ventricular pace Vp event threshold, No in Block 306, the device does not determine and store an interval difference factor, Block 310, for the intervals 366 formed by the current sensed events 342-348, and the process is repeated using the next sensed event 350 and the resulting next sensed event window 360.

In particular, the device determines whether only one or less of the most recent sensed event 350 in the sensed event window 360 and the previous two sensed events 346 and 348 are ventricular sensed Vp events, Block 306. In the example illustrated in FIG. 5, the most recent sensed event 350 is a ventricular sense Vs event and both of the previous two sensed events 346 and 348 are ventricular pace Vp events, resulting in there being two ventricular pace Vp events occurring during the sensed event window 360. As a result, the number of ventricular pace Vp events is not less than or equal to the ventricular pace Vp event threshold, No in Block 306, and therefore the device does not store an interval difference factor associated with the intervals 366 formed by the current sensed events 344-350, and the process is repeated using the next sensed event 352 and the resulting next sensed event window 362.

In particular, the device determines whether only one or less of the most recent sensed event 352 in the sensed event window 362 and the previous two sensed events 348 and 350 are ventricular sensed Vp events, Block 306. In the example illustrated in FIG. 5, the most recent sensed event 352 and one sensed event 350 of the two previous sensed events 348 and 350 are ventricular sense Vs events, and the other previous sensed event 348 is a ventricular pace Vp event, resulting in only one ventricular pace Vp event occurring during the sensed event window 362. As a result, the number of ventricular pace VP events is less than or equal to the ventricular pace Vp event threshold, Yes in Block 306, and therefore the device determines whether the RR intervals 366 associated with the current sensed events 346-352 are greater than the interval threshold, Block 308. If the RR intervals 366 are not greater than the interval threshold, No in Block 308, the device does not store an interval difference factor, Block 310, associated with the intervals 366 formed by the current sensed events 346-352, and the process is repeated using the next sensed event 354 and the resulting next sensed event window 364.

If each of the RR intervals 366 are greater than the interval threshold, Yes in Block 308, the device stores an interval difference factor, Block 310, associated with the intervals 366 formed between the current sensed events 346-352, described below. Assuming the timer has not expired, No in Block 312, the process is then repeated using the next sensed event 354 and the resulting next sensed event window 364. If the timer has expired, Yes in Block 312, the device determines an atrial fibrillation AF score, Block 314, based on the determined RR interval difference factors, Block 310, resulting from multiple sensed event windows over the predetermined time period of Block 312, i.e., two minutes for example. The determination of the AF score is described below, with the device making a determining of either an atrial fibrillation AF event or a non-atrial fibrillation event occurring based on a comparison of the AF score to an AF detection threshold. The counters are then cleared, Block 316, and the device determines the next sensed event, Block 300, and the process is repeated for the next time period using the next sensed events and the resulting next sensed event windows, and so on.

In the example illustrated in FIG. 5, the most recent sensed event 354 and both of the two previous sensed events 350 and 352 are ventricular sense Vs events, resulting in the number of ventricular pace VP events being less than or equal to the ventricular pace Vp event threshold, Yes in Block 306. Assuming that each of the RR intervals 366 are greater than the interval threshold, Yes in Block 308, the device determines and stores an interval difference factor, Block 310, associated with the intervals 366 formed between the current sensed events 348-354, described below. In this way, assuming the timer has expired, Yes in Block 312, in the example of FIG. 5, the device determines and stores an interval difference factor, Block 310, only for intervals formed in sensed event windows 356, 362 and 364, and not for intervals formed in sensed event windows 358 and 360. The determination of the atrial fibrillation AF score, Block 314, described below, is therefore made based on the interval difference factor, Block 310, determined only for intervals formed in sensed event windows 356, 362 and 364, and therefore does not include intervals formed in sense event windows 358 and 360 having more than the predetermined number of ventricular pace Vp events therein.

Figure 6:
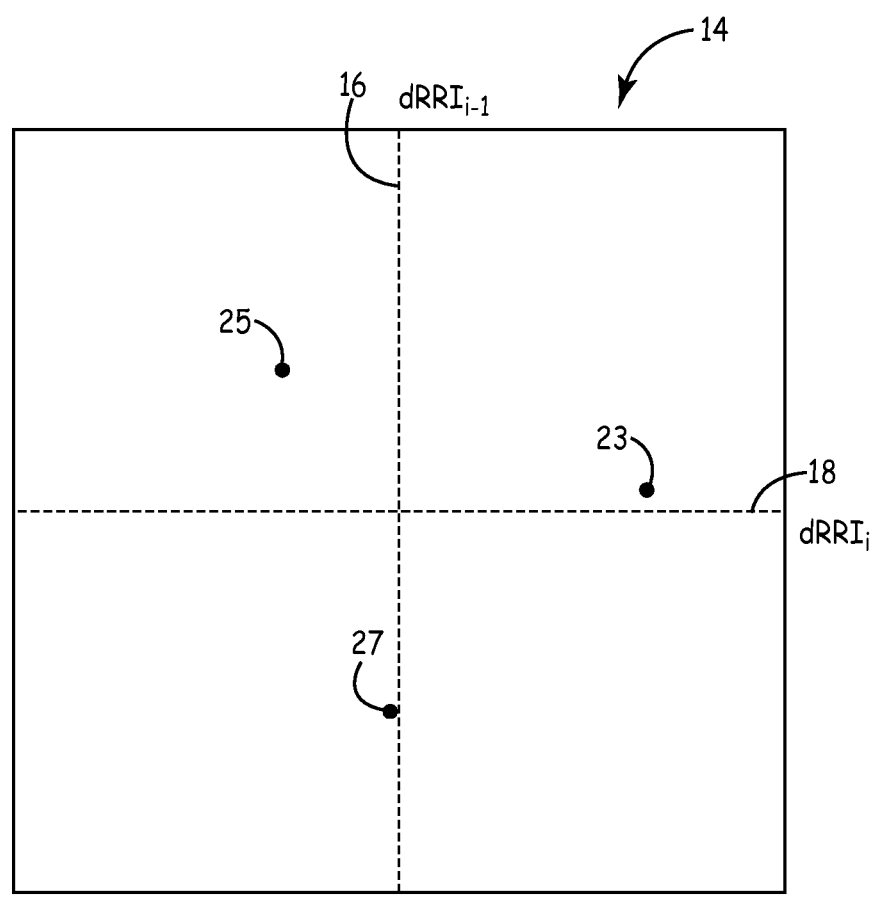
FIG. 6 is a schematic diagram of classifying of cardiac events in a cardiac medical device according to an embodiment of the present disclosure.

FIG. 6 is a schematic diagram of classifying of cardiac events in a cardiac medical device according to an embodiment of the present disclosure. As illustrated in FIG. 6, according to one embodiment, in order to determine the atrial fibrillation AF score based on the determined RR intervals difference factors resulting from multiple sensed event windows, described above, the determined RR interval difference factors calculated for the RR intervals formed by the sensed events for each sensed event window, described above, are used to plot single points on a Lorentz plot 14.

The Lorenz plot 14 is a Cartesian coordinate system defined by $\delta RR_i$ along the x-axis 18 and $\delta RR_{i-1}$ along the y-axis 16. As such, each plotted point in a Lorenz plot is defined by an x-coordinate equaling $\delta RR_i$ and a y-coordinate equaling $\delta RR_{i-1}$. $\delta RR_i$ is the difference between the $i^{th}$ RR interval and the previous RR interval, $RRI_{i-1}$. $\delta RR_{i-1}$ is the difference between and the previous RR interval, $RRI_{i-2}$. As such, each data point plotted on the Lorenz plot 14 represents a ventricular cycle length VCL pattern relating to three consecutive VCLs: $RRI_i$, $RRI_{i-1}$ and $RRI_{i-2}$, measured between the four consecutively sensed R-waves associated with a sensing event window.

In order to plot each point on the Lorenz plot area 14, a ($\delta RR_i$, $\delta RR_{i-1}$) point is identified based on the RR interval difference determined for the intervals formed by the sensed events in each single sensed event window during the two minute time period having one or less ventricular pace Vp events, described above. The atrial fibrillation AF score for each two minute time period is then determined based on the relative position of the resulting plotted points on the plot area 14. For example, using the example illustrated in FIG. 5, a first data point 23 is plotted based on the RR interval difference factor determined for intervals 366 formed in sensed event window 356, a second data point 25 is plotted based on the RR interval difference factor determined for intervals 366 formed in sensed event window 362, and a third data point 27 is plotted based on the RR interval difference factor determined for intervals 366 formed in sensed event window 364, and so forth.

In particular, for example, $\delta RR_i$ for the first data point 23 is determined as the difference between the RR interval 366 between sense 346 and sense 344 and the RR interval 366 between sense 344 and sense 342, and $\delta RR_{i-1}$ is determined as the difference between the RR interval 366 between sense 344 and sense 342 and the RR interval 366 between sense 342 and sense 340. In the same way, the corresponding ($\delta RR_i$, $\delta RR_{i-1}$) point is identified for sensed event windows 362 and 364, and so on until the timer has expired.

The plotted ($\delta RR_i$, $\delta RR_{i-1}$) points over a two minute time period are then used to identify the event as either an atrial fibrillation event or a non-atrial fibrillation. Methods have been developed for detecting atrial arrhythmias based on the irregularity of ventricular cycles measured by RR intervals that exhibit discriminatory signatures when plotted in a Lorenz scatter plot such as the plot shown in FIG. 6. One such method is generally disclosed by Ritscher et al. in U.S. Pat. Nos. 7,031,765, or in 8,639,316 to Sarkar, both incorporated herein by reference in their entireties. Other methods are generally disclosed by Sarkar, et al. in U.S. Pat. Nos. 7,623,911 and in 7,537,569 and by Houben in U.S. Pat. No. 7,627,368, all of which patents are also incorporated herein by reference in their entirety.

Figure 7:
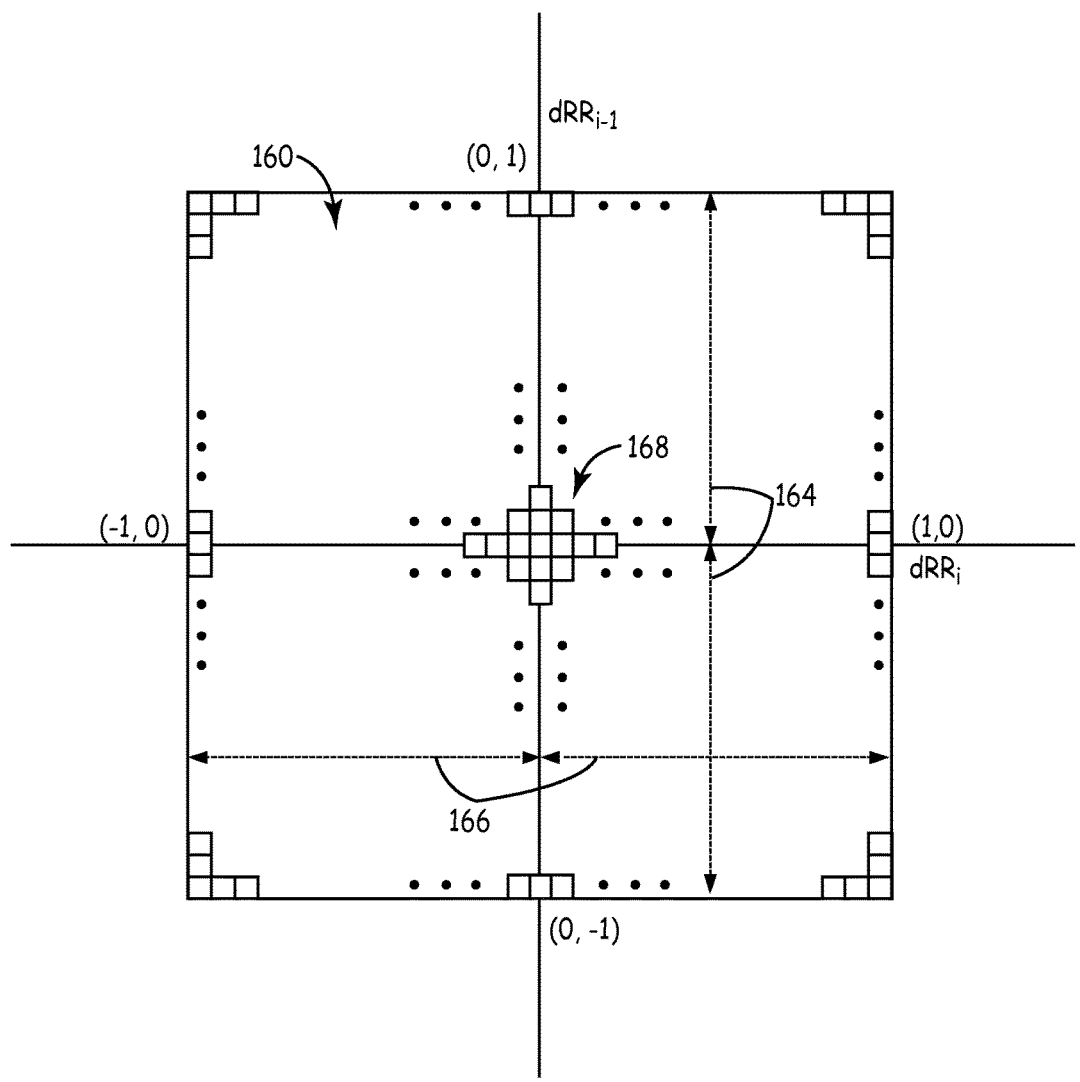
FIG. 7 is a diagram of an exemplary two-dimensional histogram representing a Lorenz plot area for identifying cardiac events.

FIG. 7 is a diagram of an exemplary two-dimensional histogram representing a Lorenz plot area for identifying cardiac events. Generally, the Lorenz plot area 14 shown in FIG. 7 is numerically represented by a two-dimensional histogram 160 having predefined ranges 166 and 164 in both positive and negative directions for the $\delta RR_i$ and $\delta RR_{i-1}$ coordinates, respectively. The two-dimensional histogram is divided into bins 168 each having a predefined range of $\delta RR_i$ and $\delta RR_{i-1}$ values. In one example, the histogram range might extend from −1200 ms to +1200 ms for both $\delta RR_i$ and $\delta RR_{i-1}$ values, and the histogram range is divided into bins extending 7.5 ms in each of the two dimensions resulting in a 160 bin×160 bin histogram. The successive RRI differences determined over a detection time interval are used to populate the histogram 160. Each bin stores a count of the number of ($\delta RR_i$, $\delta RR_{i-1}$) data points falling into the bin range. The bin counts may then be used in determining RRI variability metrics and patterns for determining a cardiac rhythm type.

An RRI variability metric is determined from the scatter plot. Generally, the more histogram bins that are occupied, i.e. the more sparse the distribution of $(\delta RR_i, \delta RR_{i-1})$ points, the more irregular the VCL during the data acquisition time period. As such, a metric of the RRI variability can be used for detecting atrial fibrillation, which is associated with highly irregular VCL. In one embodiment, an RRI variability metric for detecting AF, referred to as an AF score is computed as generally described in the above-incorporated '911 patent. Briefly, the AF score may be defined by the equation:

AF Evidence=Irregularity Evidence−Origin Count−PAC Evidence wherein Irregularity Evidence is the number of occupied histogram bins outside a Zero Segment defined around the origin of the Lorenz plot area. During normal sinus rhythm or highly organized atrial tachycardia, nearly all points will fall into the Zero Segment because of relatively small, consistent differences between consecutive RRIs. A high number of occupied histogram bins outside the Zero segment is therefore positive evidence for AF.

The Origin Count is the number of points in a "Zero Segment" defined around the Lorenz plot origin. A high Origin Count indicates regular RRIs, a negative indicator of atrial fibrillation, and is therefore subtracted from the Irregularity Evidence term. In addition, a regular PAC evidence score may be computed as generally described in the above-incorporated '911 patent. The regular PAC evidence score is computed based on a cluster signature pattern of data points that is particularly associated with PACs that occur at regular coupling intervals and present regular patterns of RRIs, e.g. associated with bigeminy (short-short-long RRIs) or trigeminy (short-short-short-long RRIs).

In other embodiments, an AF score or other RRI variability score for classifying an atrial rhythm may be computed as described in any of the above-incorporated '765, '316, '911, '569 and '368 patents.

The AF score is compared to an AF threshold for detecting atrial fibrillation to determine whether the AF score corresponds to an AF event. The AF threshold may be selected and optimized based on historical clinical data of selected patient populations or historical individual patient data, and the optimal threshold setting may vary from patient to patient. If the metric crosses a detection threshold, AF detection occurs. A response to AF detection is made, either in response to a classification of a single two second time interval as being AF, i.e., being greater than the AF threshold, or in response to a predetermined number of two second intervals being classified as being an AF event by each being greater than the AF threshold. Such response to the AF detection may include withholding or altering therapy, such as a ventricular therapy, for example, storing data that can be later retrieved by a clinician, triggering an alarm to the patient or that may be sent remotely to alert the clinician, delivering or adjusting a therapy, and triggering other signal acquisition or analysis.

The RRI measurements may continue to be performed after an AF detection to fill the histogram during the next detection time interval. After each detection time interval, the RRI variability metric is determined and the histogram bins are re-initialized to zero for the next detection time interval. The new RRI variability metric determined at the end of each data acquisition interval may be used to determine if the AF episode is sustained or terminated.

Figure 8:
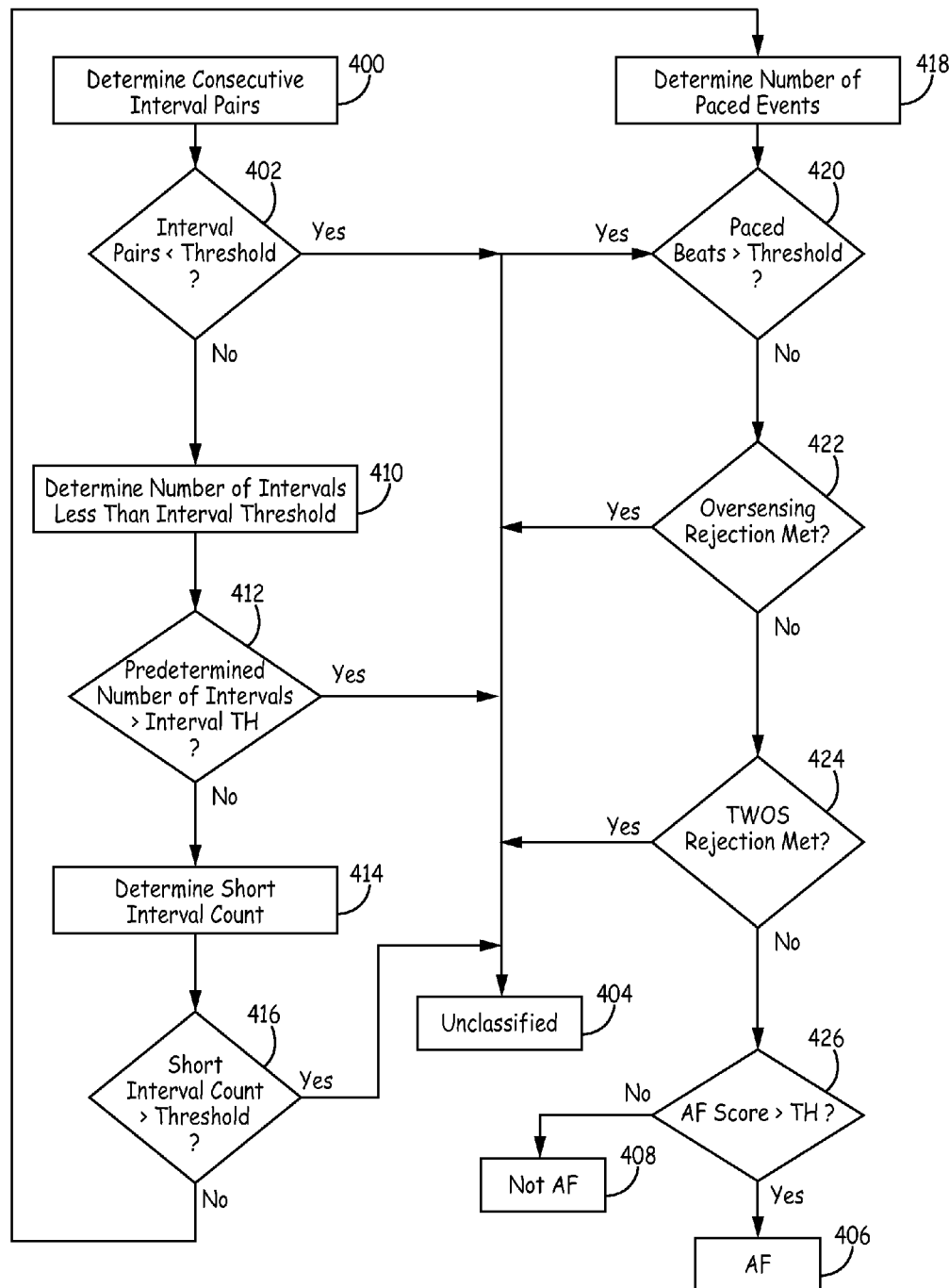
FIG. 8 is a flowchart of classification of an arrhythmia according to an embodiment of the disclosure.

FIG. 8 is a flowchart of classification of an arrhythmia according to an embodiment of the disclosure. According to another embodiment, once the two minute time period has expired and the plot has been populated with a point associated with each determined RR interval difference factor determined based on the intervals in each sensed event window occurring during the two minute time period, the device determines whether to classify the event during that two minute time period as being either an atrial fibrillation AF event, a non-atrial fibrillation event, or an unclassified event. For example, the device may look at any one or more of several factors, in any combination or particular order, to determine that the event should be determined to be an unclassified event, i.e., that the event can neither be classified as an AF event or a non-AF event. Therefore, as illustrated in FIGS. 3 and 8, the device may determine the number of valid RR interval pairs, i.e., three valid consecutive RR intervals, formed between the predetermined number of sensed events that were generated during the two minute time period, Block 400. In particular, the device determines the number of sensed event windows containing three consecutive RR intervals that were formed in Block 304 during the two minute time period, Block 312.

A determination is then made as to whether the total number of valid three consecutive RR intervals formed during the two minute time period is greater than an interval pair threshold, Block 402. According to an embodiment, the predetermined number of valid interval pairs is set as 30 valid interval pairs. If the number of sensed event windows that are formed during the two minute time period is less than the interval pair threshold, Yes in Block 402, meaning less than 30 sensed event windows were determined during the two minute time period, and therefore less than 30 interval difference factors were determined in Block 310 during the two minute time interval, resulting in the plot being populated with less than 30 points (assuming the RR interval threshold is also satisfied in Block 308), the two minute time period is determined to be unclassified, Block 404.

If the number of sensed event windows that are formed during the two minute time period is not less than 30, No in Block 402, meaning 30 or more sensed event windows were determined during the two minute time period, and therefore 30 or more interval difference factors were determined in Block 310 during the two minute time interval, resulting in the plot being populated with 30 or more points, the interval pairs factor is determined not to be satisfied as an indication of the two minute time interval being unclassified.

According to another embodiment, the device may determine the total number of RR intervals that were determined to be less than the interval threshold in Block 308 during the two minute time period, Block 410, either alone or in combination with one or more other factors. The device determines whether a predetermined number of RR intervals were determined to be greater than the RR interval threshold during the two minute time period, Block 412, such as 10 RR intervals, for example. If more than 10 RR intervals of the total number of RR intervals that were determined during the two minute time period were greater than the RR interval threshold, Yes in Block 412, the interval length factor is determined to be satisfied and the two minute time period is determined to be unclassified, Block 404. If 10 RR intervals or less were greater than the RR interval threshold during the two minute time period, No in Block 412, the interval length factor is determined not to be satisfied as an indication of the two minute time interval being unclassified.

In order to classify the two minute time period, the device may also determine a short interval count of the total number of RR intervals from all of the sensing windows obtained during the two minute time period that were less than or equal to a predetermined short interval rate, Block 414, such as 120 milliseconds or 130 milliseconds, for example. The device determines whether the short interval count is greater than a short interval rate threshold, Block 416, such as 5 short intervals for example.

If the determined short interval count is greater than the short interval rate threshold, Yes in Block 416, the short interval count factor is satisfied as an indication of the two minute time interval being unclassified and therefore the two minute time interval is determined to be unclassified, Block 404. On the other hand, if the determined short interval count is not greater than the short interval rate threshold, No in Block 416, the short interval count is determined not to be satisfied as an indication of the two minute time interval being unclassified.

The device may also determine the number of sensed events, sensed during the total two minute time period within all of the sensed event windows that were determined to be ventricular pace Vp events, Block 418. A determination is made as to whether the determined number of ventricular pace Vp sensed during the two minute time interval is greater than a total ventricular pace Vp event threshold, Block 420. According to one embodiment, the total ventricular pace Vp threshold is set as 30 ventricular pace Vp events, for example.

If the number of ventricular pace Vp sensed during the two minute time interval is greater than the total ventricular pace Vp event threshold, Yes in Block 420, the ventricular pace factor is satisfied as an indication of the two minute time interval being unclassified and therefore the two minute time interval is determined to be unclassified, Block 404. On the other hand, if the determined short interval count is not greater than the short interval rate threshold, No in Block 416, the short interval count is determined not to be satisfied as an indication of the two minute time interval being unclassified.

The device may also determine whether a determination of oversensing caused by noise was met, or in process during the two minute time period, Block 422. The determination of oversensing may be performed by the device using any known oversensing determination scheme, such as the oversensing determination describe in U.S. Pat. No. 7,333,855 to Gunderson et. al., incorporated herein by reference in its entirety. If a determination of oversensing was met or was in process during the two minute time period, Yes in Block 422, the oversensing factor is satisfied as an indication of the two minute time interval being unclassified and therefore the two minute time interval is determined to be unclassified, Block 404. If a determination of oversensing was not met or was not in process during the two minute time period, No in Block 422, the oversensing factor is not satisfied as an indication of the two minute time interval being unclassified.

Finally, the device may determine whether a determination of T-wave oversensing was met or in process during the two minute time period, Block 424. The determination of T-wave oversensing may be performed by the device using any known T-wave oversensing determination scheme, such as the T-wave oversensing determination describe in U.S. Pat. No. 7,831,304 to Gillberg, et al., incorporated herein by reference in its entirety. If a determination of T-wave oversensing was met or was in process during the two minute time period, Yes in Block 424, the T-wave oversensing factor is satisfied as an indication of the two minute time interval being unclassified and therefore the two minute time interval is determined to be unclassified, Block 404. If a determination of T-wave oversensing was not met or was not in process during the two minute time period, No in Block 424, the T-wave oversensing factor is not satisfied as an indication of the two minute time interval being unclassified.

In this way, the device may use one or more of the described factors, which if satisfied would cause the device to determine the two minute time period as being unclassified, and if at least one the described factors for identifying the two minute time period as being unclassified are met, the two minute time period is identified as being unclassified, Block 426. If none of the factors are satisfied, the AF score is determined based on the populated plot, and a determination is made as to whether the AF score is greater than an AF threshold, Block 426, as described above. If the AF score is greater than the AF threshold, Yes in Block 426, the event for the two minute period is classified as an AF event, Block 406. On the other hand, if the AF score is not greater than the AF threshold, No in Block 426, the event for the two minute period is classified as a non AF event, Block 408.

It is understood that the determination of whether the event is an unclassified event, Block 404, or an atrial fibrillation event, Block 406 or a non-atrial fibrillation event, Block 408, may be made in any order, or at the same time, so that the determination of the two minute time period as being an unclassified event may be used to override an initial determination of the two minute time period as being either an atrial fibrillation event or a non-atrial fibrillation event, or made prior to determining the two minute time period as an atrial fibrillation event or a non-atrial fibrillation event.

Figure 9:
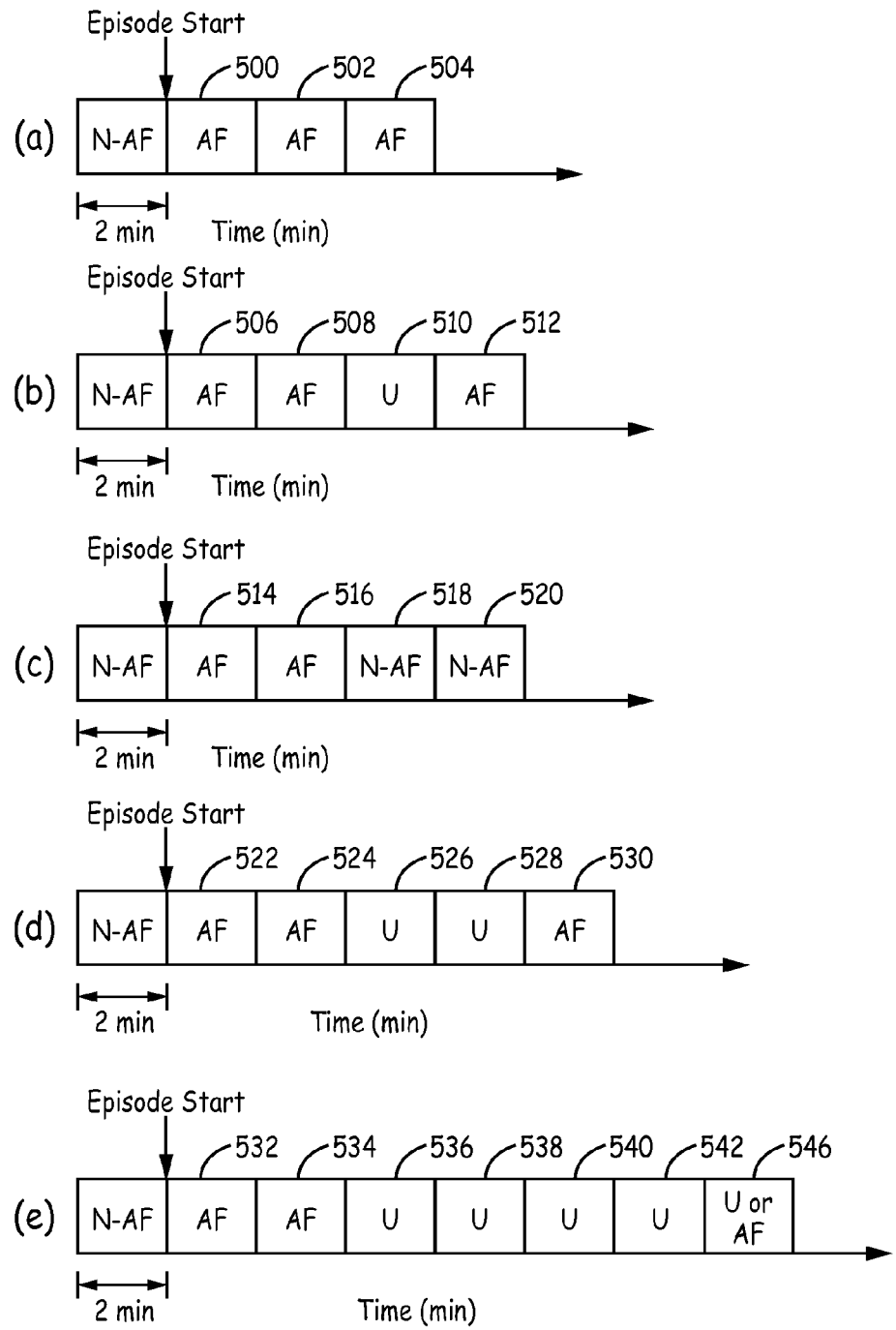
FIG. 9 is a schematic diagram of determination of a cardiac event, according to the present disclosure.

FIG. 9 is a schematic diagram of determination of a cardiac event, according to the present disclosure. As illustrated in FIG. 9, the device identifies each two minute interval as being either an AF event, a non AF event or an unclassified event using the method above in FIG. 8, and utilizes the identifications resulting for the two minute time periods to detect an AF episode. For example, once a predetermined number of two second windows, such as three, for example, have been identified as an AF event, the device determines that an atrial fibrillation episode is occurring. Therefore, as illustrated in the scenario of timing diagram (a) of FIG. 9, once the three two minute time intervals, 500-504, are classified as an AF event, the device determines that atrial fibrillation is detected. However, in the scenario illustrated in timing diagram (b), two consecutive two minute intervals 506 and 508 are identified as being AF events, a subsequent two minute time interval 510 is identified as being unclassified, which is followed by a subsequent interval 512 being identified as an AF event. According to an embodiment, the device may ignore the unclassified two minute time interval 510 and determine an AF episode once the third time interval 512 identified as AF occurs, so that an AF episode may be identified despite intermittent unclassified two minute time intervals occurring.

As illustrated in the timing diagram of scenario (c), during the determination of whether the predetermined number of two second windows are identified as AF events, the device updates an AF event counter each time an AF event is determined. For example, at the identification of two minute interval 514, the AF event counter is increment to one, and at the identification of subsequent two minute interval 514, the AF event counter is incremented to two. If two minute interval 518 were also identified as an AF event, the device would determine an AF episode, since three two minute intervals identified as an AF event would have occurred. However, since two minute interval 518 was identified as a non-AF event, the episode is determined to have terminated, and the AF counter is reset to zero, and the process continues with the next two second time interval 520. In the timing diagram of scenario (c), at the identification of two minute interval 506, the AF event counter is increment to one, at the identification of subsequent two minute interval 508, the AF event counter is incremented to two, at the identification of subsequent two minute interval 510, since the event was determined to be unclassified, the event counter remains as being equal to two, and at the identification of subsequent two minute interval 512, the AF event counter is incremented to three, and an AF episode is determined.

Similarly, in the timing diagram of scenario (d), at the identification of two minute interval 522, the AF event counter is increment to one, at the identification of subsequent two minute interval 524, the AF event counter is incremented to two, at the identification of subsequent two minute intervals 526 and 528, since the event was determined to be unclassified, the unclassified event count is incremented and the AF event count remains as being equal to two, and at the identification of subsequent two minute interval 530, the AF event count is incremented to three, and an AF episode is determined.

Had any of intervals 524-530 been identified as non-AF, indicating the termination of the AF episode, the AF event counter would have been set to zero and the process repeated starting with the next classified two minute interval. However, in addition to a two minute interval being identified as a non-AF event, the episode may also be determined to have terminate and the AF count is reset to zero if a predetermined number of two minute time periods are identified as unclassified, such as five two minute time periods, for example. Therefore, as illustrated in the timing diagram of scenario (e), at the identification of two minute interval 532, the AF event count is increment to one, at the identification of subsequent two minute interval 534, the AF event count is incremented to two, at the identification of the four subsequent two minute intervals 536-542, since the event was determined to be unclassified, the AF event count remains equal to two. If the subsequent two minute interval 544 is determined to either unclassified or a non-AF event, the AF episode would be determined to have terminated and the AF event counter would be set to zero and the process repeated starting with the next classified two minute interval. If two minute time period 546 had been classified as an AF event, an AF episode would have been identified.

Figure 10:
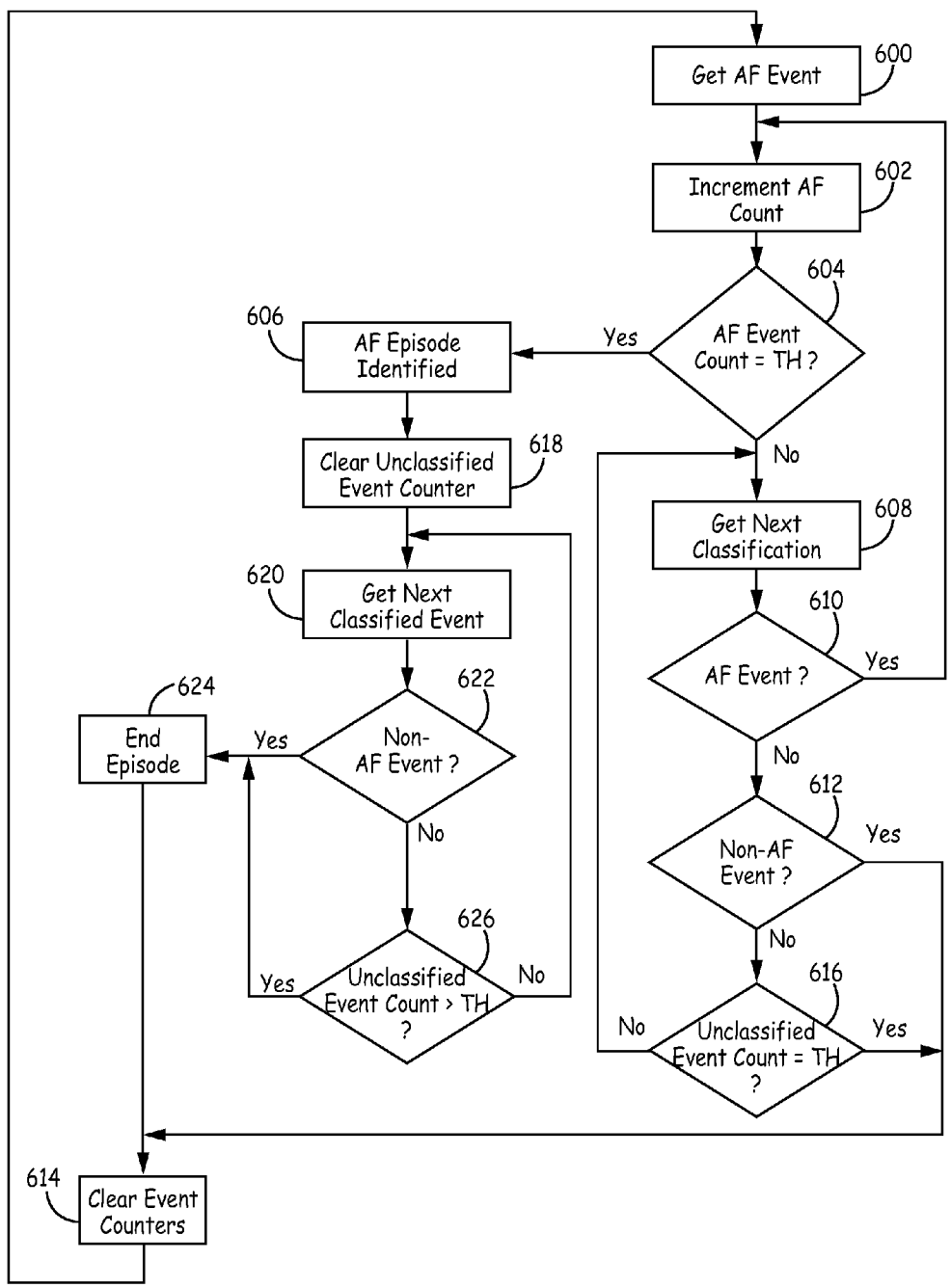
FIG. 10 is a flowchart of determination of a cardiac episode, according to an embodiment of the disclosure.

FIG. 10 is a flowchart of determination of a cardiac episode, according to an embodiment of the disclosure. As illustrated in FIGS. 9 and 10, during identification of two minute intervals as being either an AF event, a non AF event or an unclassified event using the method described above in FIG. 8, once the identification of a two minute time interval as an AF event occurs, Block 600, and the AF event counter is incremented, Block 602, and the device determines whether the AF event count is equal to an AF event count threshold, Block 604, such as three AF events, for example. Once the AF event count is equal to the AF event count threshold, Yes in Block 604, an AF episode is identified, Block 606. If the AF event count is not equal to the AF event count threshold, No in Block 604, the device determines, based on the next two minute time interval classification, Block 608, whether the next two minute time interval is classified as a non-AF event, Block 612. If the next two minute time interval is classified as a non-AF event, Yes in Block 612, the AF event counter and the unclassified event counter are both set to zero, Block 614, and the process repeated starting with the next classified two minute interval, Block 600.

If the next two minute time interval is not classified as a non-AF event, No in Block 612, the device determines whether the unclassified event counter is equal to the unclassified event count threshold, such as five unclassified events, for example, Block 616. If the unclassified event counter is not equal to the unclassified event count threshold, No in Block 616, the process is repeated based on the next subsequent two minute time interval classification, Block 608. If the unclassified event counter is equal to the unclassified event count threshold, Yes in Block 616, the AF event counter and the unclassified event counter are both set to zero Block 614, and the process repeated starting with the next classified two minute interval, Block 600.

According an embodiment of the disclosure, once the AF event count is equal to the AF event threshold, Yes in Block 604, and therefore an AF episode is identified in Block 606, the device may determine the end of the specific AF episode. For example, at identification of an AF episode, Block 606, the unclassified event counter is set to zero, Block 618, the device determines, based on the next two minute time period classification, Block 620, whether the next two minute time interval is classified as a non-AF event, Block 622. If the next two minute time interval is classified as a non-AF event, Yes in Block 622, the episode is determine to have terminated, Block 624, and the AF event counter and the unclassified event counter are both set to zero Block 614, and the process is repeated starting with the next classified two minute interval, Block 600. If the next two minute time interval is not classified as a non-AF event, No in Block 622, the device determines whether the unclassified event counter is equal to the unclassified event count threshold, Block 626. If the unclassified event counter is not equal to the unclassified event count threshold, No in Block 626, the process is repeated based on the next subsequent two minute time period classification, Block 620. If the unclassified event counter is equal to the unclassified event count threshold, Yes in Block 626, the AF episode is determined to have terminated, Block 624, the AF event counter and the unclassified event counter are both set to zero Block 614, and the process repeated starting with the next classified two minute interval, Block 600.

According to an embodiment of the disclosure, the identification of the AF episode, along with the classification of the two minute time intervals as being either an AF event, a non-AF event, or an unclassified event are stored and may be later retrieved by a clinician, either remotely or through interrogation of the device. AF burden (e.g., an AF daily burden) may be calculated using a single two minute AF classification or a predetermined number of two minute AF classifications, such as three two minute AF classifications, for example. An alarm may be sent remotely to alert the clinician if the AF burden exceeds a predetermined threshold (e.g., one hour for example), or may be sent to notify the clinician or patient of the one or more two minute time interval classifications and/or the identification of an AF episode, when termination of the episode occurs and how it was determined to have terminated, i.e., by a non-AF two minute time period or the predetermined number of unclassified two minute time periods.

Thus, an apparatus and method have been presented in the foregoing description with reference to specific embodiments. It is appreciated that various modifications to the referenced embodiments may be made without departing from the scope of the invention as set forth in the following claims.

We claim:

1. A method of determining an atrial fibrillation (AF) episode in a medical device, comprising:
   obtaining a cardiac signal sensed via one or more electrodes;
   determining, for each of a plurality of predetermined time intervals, one or more classification factors associated with the cardiac signal sensed during each of the respective plurality of predetermined time intervals;
   identifying, for each of the plurality of predetermined time intervals, the cardiac signal sensed during each of the respective plurality of predetermined time intervals as one of an AF event, a non-AF event, or an unclassified event based on the one or more determined classification factors;
   determining a number of the plurality of predetermined time intervals identified as AF events;
   determining a number of the plurality of predetermined time intervals identified as unclassified events;
   determining that the AF episode is occurring in response to both the number of the plurality of predetermined time intervals identified as AF events being greater than or equal to an AF event count threshold and, concurrently, the number of the plurality of predetermined time intervals identified as unclassified events being less than an unclassified event count threshold; and
   providing an indication of the occurrence of the AF episode to a user.

2. The method of claim 1, further comprising:
   determining, subsequent to the determining the AF episode to be occurring, whether a number of subsequent ones of the plurality of predetermined time intervals identified as unclassified events are equal to the unclassified event count threshold; and
   determining termination of the AF episode in response to the determined number of subsequent ones of the plurality of predetermined time intervals identified as unclassified events being equal to the unclassified event count threshold.

3. The method of claim 1, wherein the AF event count threshold comprises three predetermined time intervals identified as AF events and the unclassified event count threshold comprises five predetermined time intervals identified as unclassified events.

4. The method of claim 1, further comprising:
   identifying a first one of the plurality of predetermined time intervals as a first AF event;
   identifying a second one of the plurality of predetermined time intervals subsequent to the first one of the plurality of predetermined time intervals as a second AF event;
   identifying a third one of the plurality of predetermined time intervals subsequent to the second one of the plurality of predetermined time intervals as an unclassified event;
   identifying a fourth one of the plurality of predetermined time intervals subsequent to the third one of the plurality of predetermined time intervals as a third AF event; and
   determining that the AF episode is occurring in response to identifying the third AF event.

5. The method of claim 4, further comprising:
   determining, subsequent to the determining the AF episode to be occurring, whether a number of subsequent ones of the plurality of predetermined time intervals identified as unclassified events are equal to the unclassified event count threshold; and
   determining termination of the AF episode in response to the determined number of subsequent ones of the plurality of predetermined time intervals identified as unclassified events being equal to the unclassified event count threshold.

6. The method of claim 1, further comprising:
   detecting a plurality of sensed ventricular events in the sensed cardiac signal;
   determining a plurality of sensed event windows, each of the plurality of sensed event windows including a predetermined number of the sensed ventricular events;
   determining, for each of the plurality of sensed event windows, whether a number of sensed ventricular events corresponding to paced events within the sensed event window is less than a window paced event threshold;
   determining whether RR intervals within the sensed event windows having a number of sensed ventricular events corresponding to paced events less than the window paced event threshold are greater than a window interval threshold;
   determining RR interval differences for each of the plurality of sensed event windows in which each of the RR intervals are greater than the window interval threshold; and
   wherein identifying, for each of the plurality of predetermined time intervals, the cardiac signal sensed during each of the respective plurality of predetermined time intervals as one of an AF event, a non-AF event, or an unclassified event based on the one or more determined factors comprises identifying, for each of the plurality of predetermined time intervals, the cardiac signal sensed during each of the respective plurality of predetermined time intervals as one of an AF event, a non-AF event, or an unclassified event based at least on the RR interval differences.

7. The method of claim 6, wherein
   determining classification factors in response to the sensed cardiac signal comprises:
   determining sensed event windows having predetermined interval pairs in response to the sensed cardiac signal during a predetermined time period;
   determining whether a number of the determined sense event windows is less than an interval pair threshold;
   determining whether a number of intervals occurring during the predetermined time period and not within the sensed event windows that are less than a predetermined interval threshold is greater than a sensed interval threshold;
   determining whether a predetermined number of intervals occurring during the predetermined time period and not within the sensed event windows are less than a short interval count threshold;
   determining whether a predetermined number of intervals occurring during the predetermined time period that are either within the sensed event windows or not within the sensed event windows that are paced events is greater than a paced event threshold; and
   determining whether oversensing detection occurred during the predetermined event time period.

8. The method of claim 1, further comprising:
   determining, subsequent to determining the AF episode to be occurring, that a subsequent one of the plurality of predetermined time intervals is identified as a non-AF event; and
   determining termination of the AF episode in response to determining, subsequent to determining the AF episode to be occurring, that the subsequent one of the plurality of predetermined time intervals is identified as the non-AF event.

9. A medical device for determining an atrial fibrillation (AF) episode, comprising:
a sense amplifier configured to obtain a cardiac signal sensed via one or more electrodes; and
a processor configured to determine, for each of a plurality of predetermined time intervals, one or more classification factors associated with the cardiac signal sensed during each of the respective plurality of predetermined time intervals, identify, for each of the plurality of predetermined time intervals, the cardiac signal sensed during each of the respective plurality of predetermined time intervals as one of an AF event, a non-AF event, or an unclassified event based on the one or more determined classification factors, determine a number of the plurality of predetermined time intervals identified as AF events, determine a number of the plurality of predetermined time intervals identified as unclassified events, determine that the AF episode is occurring in response to both the number of the plurality of predetermined time intervals identified as AF events being greater than an or equal to an AF event count threshold and, concurrently, the number of the plurality of predetermined time intervals identified as unclassified events being less than an unclassified event count threshold, and provide an indication of the occurrence of the AF episode to a user.

10. The medical device of claim 9, wherein the processor is further configured to determine, subsequent to determining the AF episode to be occurring, whether a number of subsequent ones of the plurality of predetermined time intervals identified as unclassified events are equal to the unclassified event count threshold, and determine termination of the AF episode in response to the determined number of subsequent ones of the plurality of predetermined time intervals identified as unclassified events being equal to the unclassified event count threshold.

11. The medical device of claim 9, wherein the AF event count threshold comprises three predetermined time intervals identified as AF events and the unclassified event count threshold comprises five predetermined time intervals identified as unclassified events.

12. The medical device of claim 9, wherein the processor is further configured to identify one of the plurality of predetermined time intervals as a first AF event, identify one of the plurality of predetermined time intervals subsequent to the first one of the plurality of predetermined time intervals as a second AF event, identify a third one of the plurality of predetermined time intervals subsequent to the second one of the plurality of predetermined time intervals as an unclassified event, identify a fourth one of the plurality of predetermined time intervals subsequent to the third one of the plurality of predetermined time intervals as a third AF event, and determine that the AF episode is occurring in response to identifying the third AF event.

13. The medical device of claim 12, wherein the processor is further configured to determine, subsequent to the determining the AF episode to be occurring, whether a number of subsequent ones of the plurality of predetermined time intervals identified as unclassified events are equal to the unclassified event count threshold, and determine termination of the AF episode in response to the determined number of subsequent ones of the plurality of predetermined time intervals identified as unclassified events being equal to the unclassified event count threshold.

14. The medical device of claim 9, wherein the processor is further configured to detecting a plurality of sensed ventricular events in the sensed cardiac signal, determine a plurality of sensed event windows, each of the plurality of sensed event windows including a predetermined number of the sensed ventricular events, determine, for each of the sensed event windows, whether a number of sensed ventricular events corresponding to paced events within the sensed event window is less than a window paced event threshold, determine whether RR intervals within the sensed event windows having a number of sensed ventricular events corresponding to paced events less than the window paced event threshold are greater than a window interval threshold, determine RR interval differences for each of the plurality of sensed event windows in which each of the RR intervals are greater than the window interval threshold, and identify the cardiac signal sensed during each of the respective plurality of predetermined time intervals as one of an AF event, a non-AF event, or an unclassified event based at least on the RR interval differences.

15. The medical device of claim 14, wherein the processor is further configured to determine the one or more classification factors by at least one of:
determining sensed event windows having predetermined interval pairs in response to the sensed cardiac signal during a predetermined time period;
determining whether a number of the determined sense event windows is less than an interval pair threshold;
determining whether a number of intervals occurring during the predetermined time period and not within the sensed event windows that are less than a predetermined interval threshold is greater than a sensed interval threshold;
determining whether a predetermined number of intervals occurring during the predetermined time period and not within the sensed event windows are less than a short interval count threshold;
determining whether a predetermined number of intervals occurring during the predetermined time period that are either within the sensed event windows or not within the sensed event windows that are paced events is greater than a paced event threshold; and
determining whether oversensing detection occurred during the predetermined event time period.

16. The medical device of claim 9, wherein the processor is further configured to determine, subsequent to determining the AF episode to be occurring, that a subsequent one of the plurality of predetermined time intervals is identified as a non-AF event, and determine termination of the AF episode in response to determining that the subsequent one of the plurality of predetermined time intervals is identified as the non-AF event.

17. The medical device of claim 9, wherein the device comprises a single-chamber implantable medical device that obtains the cardiac signal via electrodes within a ventricle of the heart.

18. A non-transitory computer-readable medium storing a set of instructions which cause a processor of a medical device to perform a method comprising:
determining an atrial fibrillation (AF) episode in a medical device, comprising:
obtaining a cardiac signal sensed via one or more electrodes;
determining, for each of a plurality of predetermined time intervals, one or more classification factors associated with the cardiac signal sensed during each of the respective plurality of predetermined time intervals;

identifying, for each of the plurality of predetermined time intervals, the cardiac signal sensed during each of the respective plurality of predetermined time intervals as one of an AF event, a non-AF event, or an unclassified event based on the one or more determined classification factors;

determining a number of the plurality of predetermined time intervals identified as AF events;

determining a number of the plurality of predetermined time intervals identified as unclassified events;

determining that the AF episode is occurring in response to both the number of the plurality of predetermined time intervals identified as AF events being greater than or equal to an AF event count threshold and, concurrently, the number of the plurality of predetermined time intervals identified as unclassified events being less than an unclassified event count threshold; and providing an indication of the occurrence of the AF episode to a user.

* * * * *